(12) United States Patent
Laird et al.

(10) Patent No.: US 7,803,131 B2
(45) Date of Patent: Sep. 28, 2010

(54) DEVICES AND METHODS FOR PERCUTANEOUSLY TREATING AORTIC VALVE STENOSIS

(75) Inventors: Rob Laird, Pinole, CA (US); Rick Helkowski, Menlo Park, CA (US)

(73) Assignee: Cordis Corporation, Miami Lakes, FL (US)

( * ) Notice: Subject to any disclaimer, the term of this patent is extended or adjusted under 35 U.S.C. 154(b) by 1027 days.

(21) Appl. No.: 11/318,058

(22) Filed: Dec. 22, 2005

(65) Prior Publication Data

US 2006/0161133 A1 Jul. 20, 2006

Related U.S. Application Data

(63) Continuation of application No. 10/893,127, filed on Jul. 16, 2004, now abandoned.

(60) Provisional application No. 60/531,473, filed on Dec. 19, 2003, provisional application No. 60/488,507, filed on Jul. 17, 2003.

(51) Int. Cl.
*A61M 29/00* (2006.01)
(52) U.S. Cl. .................. 604/101.01; 606/194
(58) Field of Classification Search ................
604/101.01–102.02, 103.07, 103.13; 606/194, 606/200
See application file for complete search history.

(56) References Cited

U.S. PATENT DOCUMENTS

| | | | |
|---|---|---|---|
| 4,573,966 A * | 3/1986 | Weikl et al. ................. 604/509 |
| 4,808,153 A | 2/1989 | Parisi | |
| 5,059,178 A | 10/1991 | Ya | |
| 5,100,425 A | 3/1992 | Fischell et al. .............. 606/159 |
| 5,432,663 A | 7/1995 | Ichiara | |
| 5,458,574 A | 10/1995 | Machold et al. ........ 604/101.03 |
| 5,538,504 A | 7/1996 | Linden et al. ............... 604/508 |
| 5,632,762 A * | 5/1997 | Myler ........................ 606/194 |
| 5,899,917 A * | 5/1999 | Edwards et al. ............. 606/195 |
| 5,941,869 A * | 8/1999 | Patterson et al. ............ 604/508 |
| 6,048,331 A | 4/2000 | Tsugita et al. ......... 604/102.03 |
| 6,231,551 B1 * | 5/2001 | Barbut ........................ 604/236 |
| 6,350,252 B2 | 2/2002 | Ray et al. .................... 604/107 |
| 6,423,032 B2 * | 7/2002 | Parodi ................... 604/103.07 |
| 6,425,916 B1 | 7/2002 | Garrison et al. ............. 623/2.11 |
| 6,527,979 B2 | 3/2003 | Constantz et al. | |
| 6,533,767 B2 | 3/2003 | Johansson et al. | |
| 2001/0016750 A1 | 8/2001 | Malecki et al. ............. 606/158 |
| 2001/0039411 A1 | 11/2001 | Johansson et al. | |
| 2004/0082910 A1 * | 4/2004 | Constantz et al. ...... 604/101.04 |

FOREIGN PATENT DOCUMENTS

| WO | WO 88/09683 A | 12/1988 |
|---|---|---|
| WO | WO 00/03651 | 1/2000 |
| WO | WO 00/03651 A1 | 1/2000 |
| WO | WO 01/13985 | 3/2001 |
| WO | WO 01/13985 A1 | 3/2001 |
| WO | WO 01/15767 | 3/2001 |
| WO | WO 01/15767 A1 | 3/2001 |

(Continued)

*Primary Examiner*—Nicholas D Lucchesi
*Assistant Examiner*—Laura A Bouchelle (57) ABSTRACT

Devices and methods for their use in percutaneously increasing the aortic valve flow of a stenotic aortic valve are provided. The subject devices include an aortic valve isolation element, a shunt element and an aortic valve flushing element. Also provided are systems and kits that include the subject devices and can be employed in practicing the subject methods. The subject devices, methods, systems and kits find use in treating conditions associated with the presence of stenotic aortic valves.

6 Claims, 6 Drawing Sheets

FOREIGN PATENT DOCUMENTS

| | | |
|---|---|---|
| WO | WO 01/39783 | 6/2001 |
| WO | WO 01/39783 A1 | 6/2001 |
| WO | WO 01/70325 A | 9/2001 |
| WO | WO 2004/039432 A | 5/2004 |

\* cited by examiner

DEVICES AND METHODS FOR PERCUTANEOUSLY TREATING AORTIC VALVE STENOSIS

CROSS-REFERENCE TO RELATED APPLICATIONS

This application claims priority (pursuant to 35 U.S.C. §119(e)) to the filing date of U.S. Provisional Patent Application Ser. No. 60/531,473 filed on Dec. 19, 2003 and to the filing date of U.S. Provisional Patent Application Ser. No. 60/488,507 filed on Jul. 17, 2003; the disclosures of which are herein incorporated by reference.

INTRODUCTION

Background of the Invention

Aortic valve stenosis refers to a disease condition characterized by a narrowing of the aortic valve. While aortic valve stenosis can results from the presence of a bicuspid valve or rheumatic fever, wear and tear of the aortic valve in the elderly is the most common cause of this condition. This latter condition is known as "senile calcific aortic stenosis." With aging, protein collagen of the valve leaflets is destroyed, and calcium is deposited on the leaflets. Once valve leaflet mobility is reduced by calcification, turbulence across the valve increases, causing scarring, thickening, and stenosis of the valve.

Symptoms and heart problems in aortic stenosis are related to the degree of narrowing of the aortic valve area. Patients with mild aortic valve narrowing may experience no symptoms. When the narrowing becomes significant (usually greater that 50% reduction in valve area), the pressure in the left ventricle increases and a pressure difference can be measured between the left ventricle and the aorta. To compensate for the increasing resistance at the aortic valve, the muscles of the left ventricle thicken to maintain pump function and cardiac output. This muscle thickening causes a stiffer heart muscle which requires higher pressures in the left atrium and the blood vessels of the lungs to fill the left ventricle. Even though these patients may be able to maintain adequate and normal cardiac output at rest, the ability of the heart to increase output with exercise is limited by these high pressures. As the disease progresses, the increasing pressure eventually causes the left ventricle to dilate, leading to a decrease in cardiac output and heart failure. Without treatment, the average life expectancy after the onset of heart failure due to aortic stenosis is between 18 to 24 months.

When symptoms of chest pain, syncope, or shortness of breath appear, the prognosis for patients with aortic stenosis without valve replacement surgery is poor. Medical therapy, such as the use of diuretics to reduce high lung pressures and remove lung fluid, can provide only temporary relief of symptoms. Patients with symptoms usually undergo cardiac catheterization. If severe aortic stenosis is confirmed, aortic valve replacement is usually recommended. The overall mortality risk for aortic valve replacement surgery is about 5%.

While effective, aortic valve replacement is not without disadvantages, where such disadvantages include the requirement of chronic anticoagulation therapy, risk of failure and requirement for replacement, and the like.

As such, there is a continued interest in the development of new protocols for treating aortic valve stenosis. Of particular interest would be the development of a percutaneous protocol that could be practiced in a 'beating-heart' setting.

Relevant Literature

See e.g., WO 01/15767; WO 01/13985; WO 00/03651; and WO 01/39783.

SUMMARY OF THE INVENTION

Devices and methods for their use in percutaneously increasing the aortic valve flow of a stenotic aortic valve are provided. The subject devices include an aortic valve isolation element, a shunt element and an aortic valve flushing element. The aortic valve isolation element is made up of a ventricular side aortic valve occlusion element and a proximal side aortic valve isolation element. The shunt element is made up of a shunt lumen that includes one or more ventricular side blood inflow ports and one or more proximal side valves that provide for one-way exit of blood from the shunt lumen into the aorta. The aortic valve flushing element is made up of a fluid introducing element and a fluid removal element. In practicing the subject methods, a stenotic aortic valve is first isolated. Next, the isolated valve is flushed with a dissolution fluid, e.g., an acidic dissolution fluid, for a period of time sufficient for the aortic valve flow of the treated valve to be increased. In certain embodiments, the valve is also contacted with a dissolution fluid attenuating fluid, e.g., a buffer, during or after the flushing step in order to limit the contact of non-valve tissue with the dissolution fluid. Also provided are systems and kits that include the subject devices and can be employed in practicing the subject methods. The subject devices, methods, systems and kits find use in treating conditions associated with the presence of stenotic aortic valves.

DETAILED DESCRIPTION OF THE INVENTION

Devices and methods for their use in percutaneously increasing the aortic valve flow of a stenotic aortic valve are provided. The subject devices include an aortic valve isolation element, a shunt element and an aortic valve flushing element. The aortic valve isolation element is made up of a ventricular side aortic valve occlusion element and a proximal side aortic valve isolation element. The shunt element is made up of a shunt lumen that includes one or more ventricular side blood inflow ports and one or more proximal side valves that provide for one-way exit of blood from the shunt lumen into the aorta. The aortic valve flushing element is made up of a fluid introducing element and a fluid removal element. In practicing the subject methods, a stenotic aortic valve is first isolated. Next, the isolated valve is flushed with a dissolution fluid, e.g., an acidic dissolution fluid, for a period of time sufficient for the aortic valve flow of the treated valve to be increased. In certain embodiments, the valve is also contacted with a dissolution fluid attenuating fluid, e.g., a buffer, during or after the flushing step in order to limit the contact of non-valve tissue with the dissolution fluid. Also provided are systems and kits that include the subject devices and can be employed in practicing the subject methods. The subject devices, methods, systems and kits find use in treating conditions associated with the presence of stenotic aortic valves.

Before the present invention is described further, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Conversely, it is contemplated that the claims may be so-drafted to exclude any optional element. This statement is intended to serve as antecedent basis for use of such exclusive terminology as "solely," "only" and the like in connection with the recitation of claim elements or by use of a "negative" limitation The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As summarized above, the subject invention provides devices and methods for increasing the aortic valve flow of a stenotic aortic valve, as well as systems and kits for use in practicing the subject methods. In further describing the invention, the subject devices are described first in greater detail, followed by a review of the subject methods, systems and kits.

Devices

The subject invention provides devices that are capable of locally flushing an aortic valve in situ with a dissolution fluid. As such, the subject devices are capable of locally flushing an aortic valve when present in a heart, where the heart is generally present in a subject or patient (host). By "locally flushing" is meant that the aortic valve and, at most, the immediately adjacent tissue structures are flushed with the fluid, but not the remainder of the heart or host in which the subject aortic valve is present. As such, the subject devices do not systemically administer the dissolution fluid, such that it contacts the vasculature of the heart/host beyond the aortic valve.

The subject devices are also characterized in that they are dimensioned to be sufficiently small for introduction into the vascular system (i.e., vasculature) from a remote location, e.g., femoral approach, so that they can be percutaneously introduced to the aortic valve.

The devices and methods of the present invention are designed to be employed in beating heart applications, by which is meant that the subject methods may be performed while the heart is still beating, i.e., where the heart has not been stopped.

As summarized above, the subject devices include an aortic valve isolation element, a shunt element and a valve flushing element. Each of these elements is now described separately in greater detail.

Valve Isolation Element

The valve isolation element of the subject devices is made up of three different sub-elements that work in concert to isolate the target aortic valve to be treated from the remainder of the heart/vasculature of the host. By "isolate" is meant that the fluid flow between the target aortic valve and the remainder of the vascular system is substantially, if not completely, inhibited. As such, the valve isolation system effectively partitions the target aortic valve from the remainder of the vasculature. The sub-elements that make up the valve isolation element are: (1) a ventricular side valve occlusion element; and (2) aortic side valve occlusion element. Each of these elements is now described in greater detail separately.

Ventricular Side Valve Occlusion Element

The ventricular side valve occlusion element serves to occlude blood flow through the aortic valve by blocking or occluding the upstream side of the valve, i.e., the ventricular side of the valve, thereby forcing blood to flow through the shunt element, described in greater detail below. This occlusion element also serves to anchor or stabilize the distal end of the device at the ventricular side of the aortic valve. This occlusion element may be any convenient type of occlusion element that can effectively occlude or block the ventricular site of the aortic valve. By effectively occlude or block is meant that fluid, e.g. blood, flow past the occlusion element upon activation is reduced by at least 95%, usually by at least 97% and more usually by at least 99%, where in preferred embodiments, fluid flow is reduced by 100% such that the fluid flow from the ventricle into the isolated valve site is substantially, if not completely, inhibited. Representative occlusion elements include inflatable balloons, expandable membranes or analogous materials that assume the form of a funnel (e.g., as shown in FIGS. 3, 4 and 5), etc.

In certain embodiments, the occlusion element is an expandable or inflatable balloon. In these embodiments where the occlusion element is a balloon, the balloon is generally an expandable balloon that is capable of going from a first, compressed state to a second, expanded state, e.g., by introduction of a fluid or gas into the interior of the balloon, e.g., via an inflation lumen in fluid communication with the interior of the balloon. While the inflatable balloon may be one that is designed to be inflated with a gas or liquid, of particular interest in many embodiments are those that are configured to be inflated with a liquid, e.g. a pH elevating solution as described in greater detail infra. Balloons suitable for use in vascular devices, e.g., catheter devices, cannula devices, etc., are well known to those of skill in the art and may be readily adapted for use in devices of the present invention.

Figure 3:
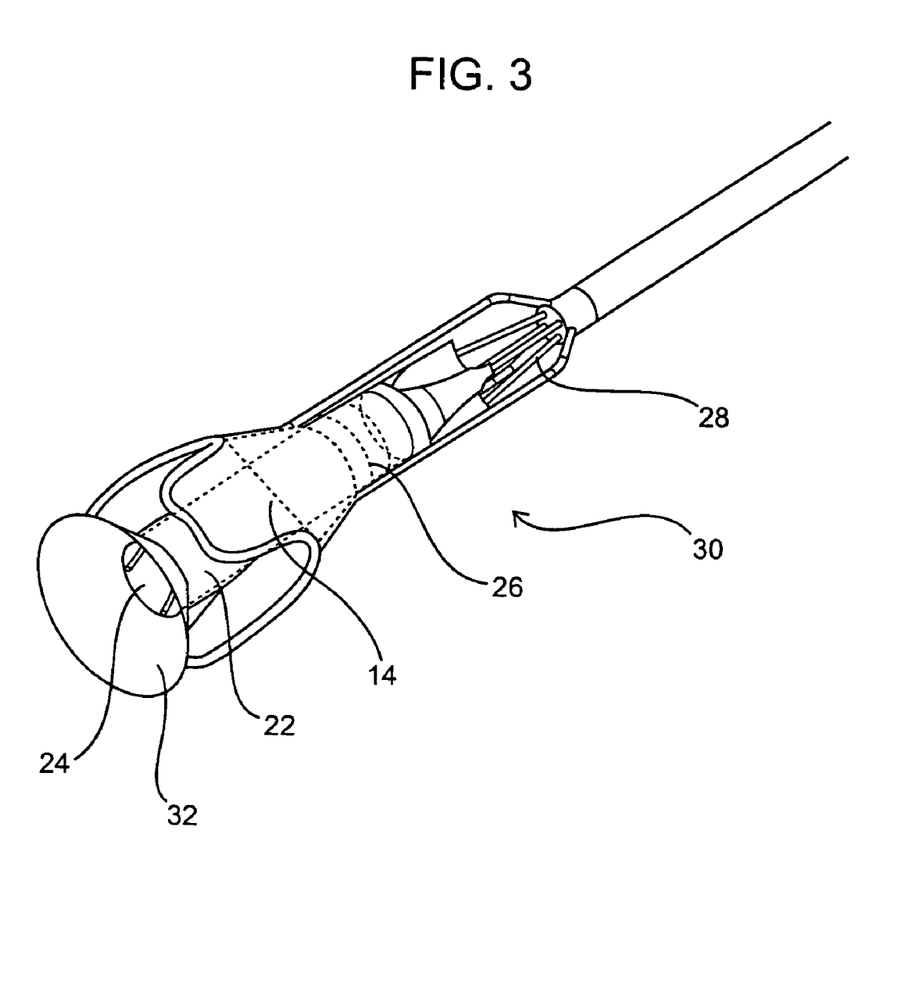
FIG. 3 provides an illustration of yet another alternative representative device configuration according to the subject invention.
Figure 4:
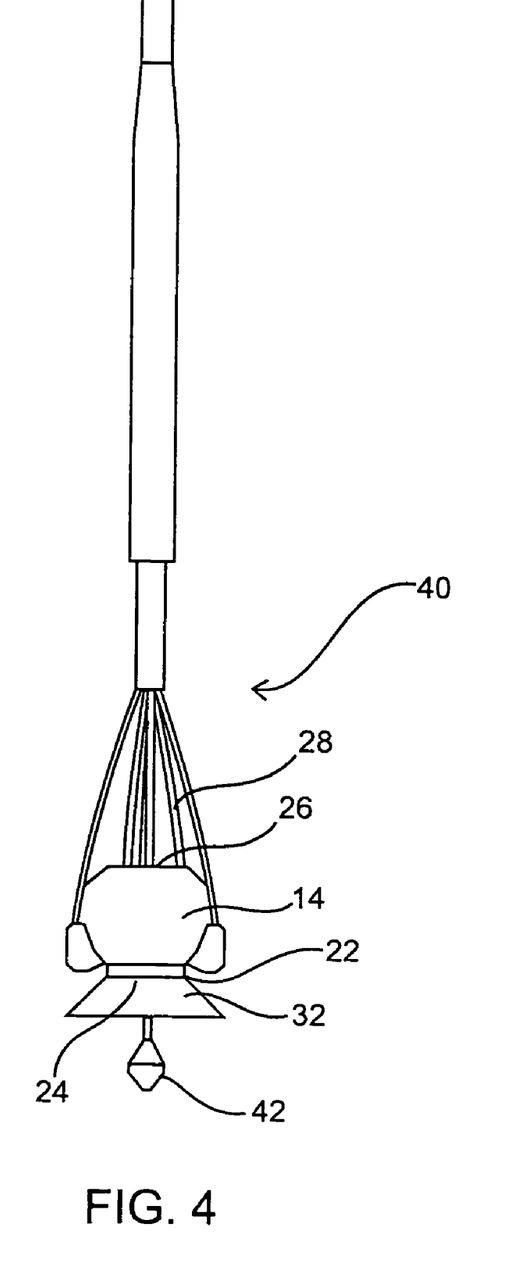
FIGS. 4 and 5 provide two different views of yet another alternative representative device configuration according to the subject invention.
Figure 5:
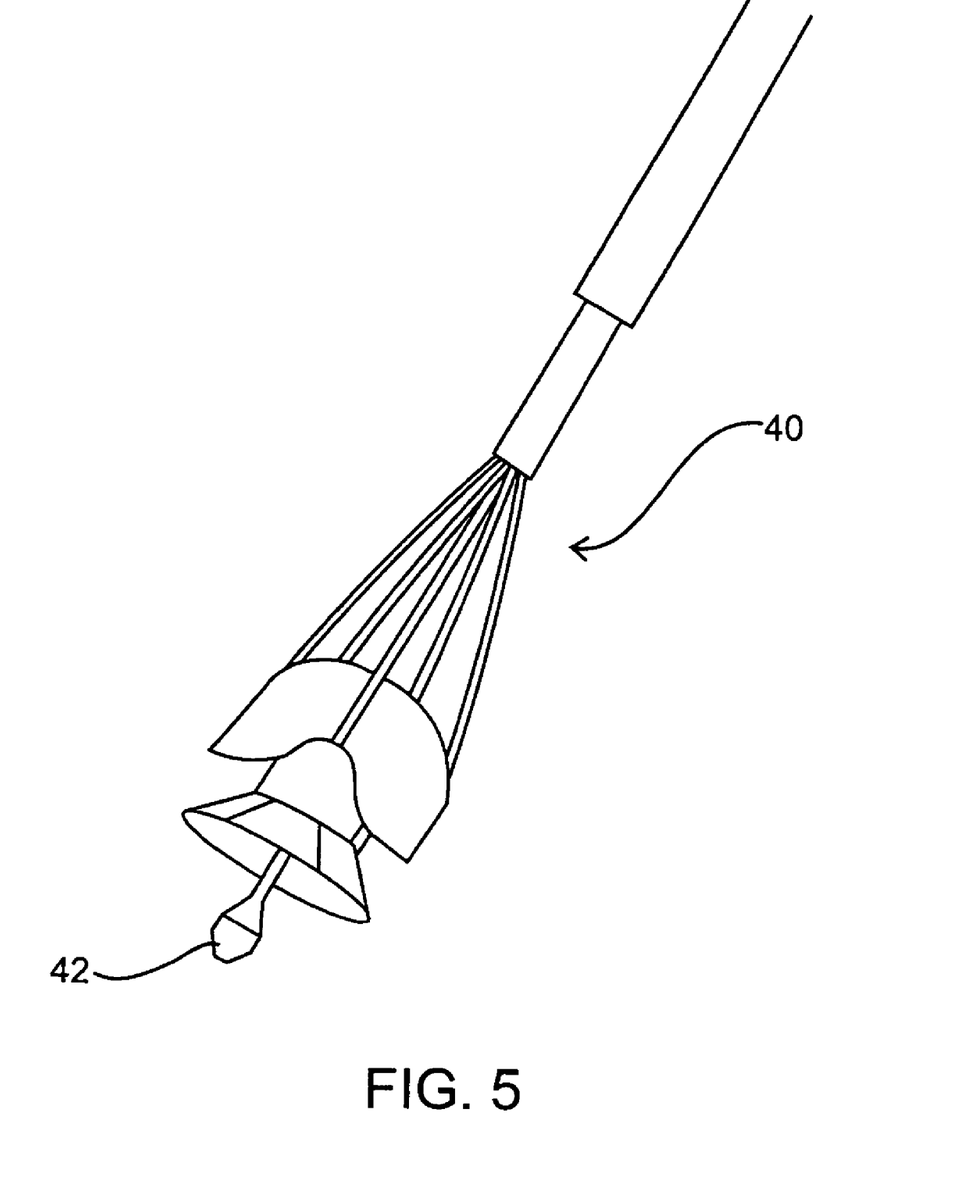

In yet other embodiments, the anchor is a structure that can assume a funnel configuration when deployed, such as is shown in FIGS. 3, 4 and 5. The funnel structure may be deployable, for example where the anchor structure uses a shape memory, e.g., NiTi, hoop attached to a thin silicone "Funnel". In such an embodiment, the funnel may be attached to the central shunt lumen. This funnel structure may then be collapsed by pulling one end of it in the longitudinal direction of the device and withdrawing the structure into the sheath. In a variation of this particular embodiment, the deployable funnel structure may be one that uses an adjustable hoop in a lasso-type configuration. Further details of such embodiments are depicted in the figures of the figures of priority provisional application Ser. No. 60/531,473, the disclosure of such details being specifically incorporated herein by reference.

Aortic Side Valve Isolation Element

The next component of the isolation system is the aortic side valve isolation element, also referred to herein as the ascending aorta occlusion element. This element serves to isolate the aortic side of the aortic valve from the remainder of the aorta and thereby prevent fluid flow from the isolated valve into the ascending aorta downstream of its deployment, as well as the coronary ostia. As such, this isolation element is one that substantially, if not completely, impedes fluid flow from the isolated region of the valve past its site of deployment downstream into the aorta, as well into the coronary ostia. The isolation element (also referred to as the "isolation bell" is, in many embodiments, an expandable element, such as the wire scaffolded membranous isolation element, as depicted in FIGS. 1 to 5. In representative embodiments, the isolation element allows for natural perfusion of the coronary arteries, such that is configured not to block the coronary arteries from blood present on the aortic side of the isolation element, e.g., blood that has been shunted from the ventricle. In certain embodiments, the isolation element has a double lip seal to provide for the desired isolation. Further details of such a double lip seal are provided in priority provisional application Ser. No. 60/531,473, the disclosure of such details being specifically incorporated herein by reference.

Shunt Element

Figure 1:
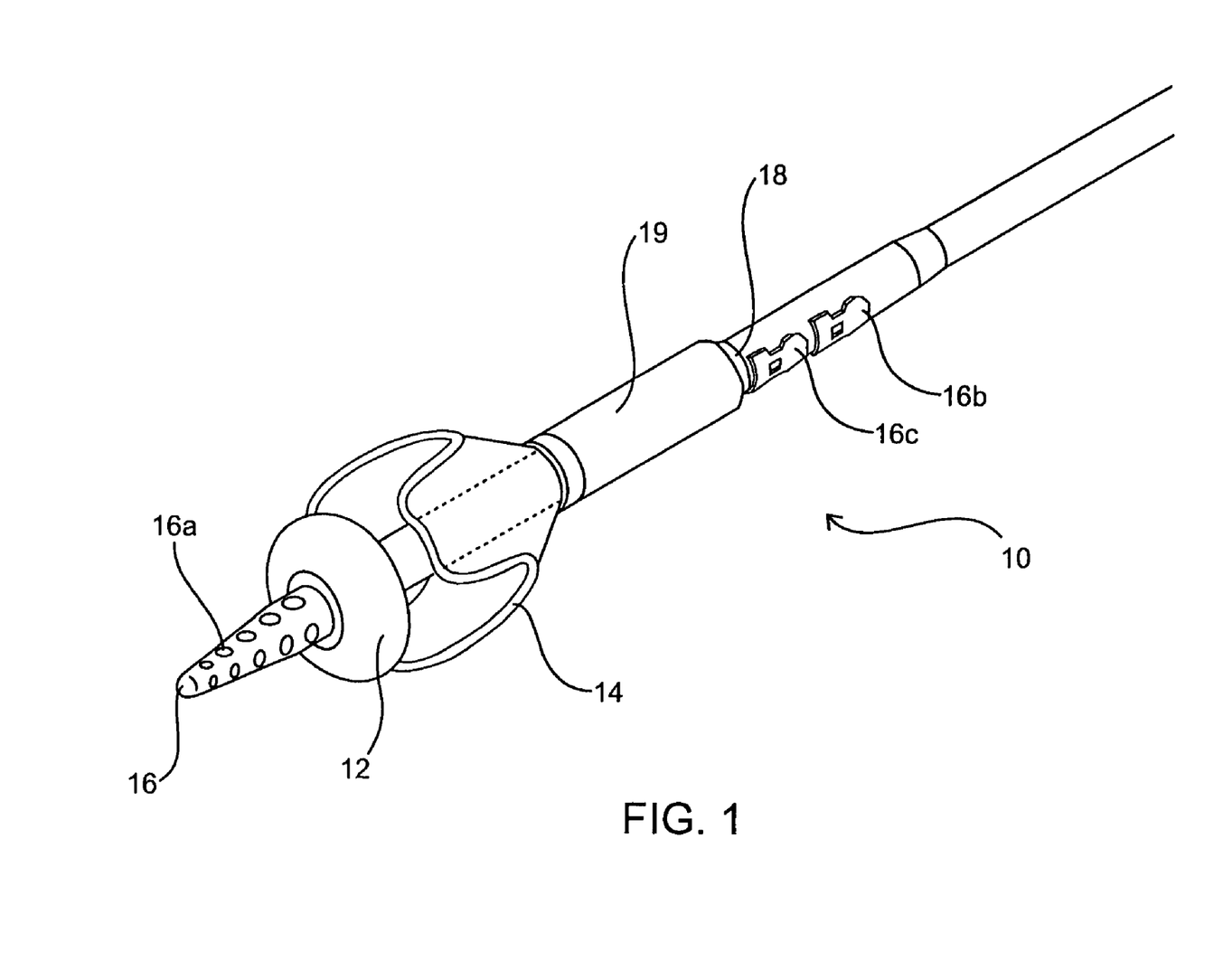
FIG. 1 provides an illustration of a representative embodiment of a device according to the subject invention.

As summarized above, the subject devices also include a shunt element that provides for blood flow through the region of isolation from the ventricular side of the valve to the aorta. Typically, the shunt is one that expands upon deployment to provide for desirable blood flow. The shunt element may be any convenient structure which provides a passageway that conveys blood from the left ventricle through the isolated area to a position downstream of the aortic side valve isolation element. In certain embodiments, this shunt element is a shunt lumen that includes one or more distal blood inflow ports and one or more proximal blood outflow ports, where the blood outflow ports may include a one-way valve component that provides for one-way fluid flow out of the shunt lumen. Such an embodiment is depicted in FIG. 1. In yet other embodiments, the shunt element may include a single, larger ventricular opening and integrated aortic valve, such as the shunt embodiment depicted in FIGS. 2 and 3.

Valve Flushing Element

Also present in the subject devices is an aortic valve flushing element for flushing an isolated aortic valve with at least a dissolution fluid. By "flushing" is meant that fresh dissolution solution is contacted with the target valve surface one or more times, including continuously, during the treatment period, as described in further detail below, where in certain representative embodiments of the subject methods, the surface of the target valve surface, typically the aortic side of the aortic valve, is continuously contacted or flushed with the dissolution fluid. In other words, the acidic dissolution fluid is introduced in a manner such that a continuous flow of the dissolution fluid across the surface of the valve is achieved.

In flushing the isolated target valve, in certain representative embodiments the pressure in the local environment which includes the isolated target valve remains substantially isometric. By substantially isometric is meant that the pressure in the local environment does not vary by a significant amount, where the amount of variance over the treatment period does not vary by more than about 50%, usually by not more than about 10% and more usually by not more than about 5%. In other words, the local environment remains substantially isobaric during the treatment period. Accordingly, the device includes a flushing element that dynamically contacts the target valve with dissolution fluid and simultaneously removes fluid from the local environment of the isolated valve, such that the overall volume of fluid in the local environment remains substantially constant, where any difference in volume at any two given times during the treatment period does not exceed about 50%, and usually does not exceed about 10%.

To provide for the above function, the flushing element of the subject devices typically includes a fluid introduction element and a fluid removal (i.e., aspiration) element, which elements are capable of introducing fluid into and removing fluid from the isolated local environment of the target aortic valve such that the aortic valve, or at least the aortic side thereof, is flushed with the introduced fluid. The fluid introduction and removal elements may take a variety of different configurations, so long as they serve their intended purpose of introducing fluid into and removing fluid from the isolated local environment of the target aortic valve. Representative configurations include, but are not limited to: two separate tubes or analogous fluid conveyance structures, where the tubes may or may not be concentric; two separate lumens of a single tube, e.g., a tube having a dividing partition running the length of the tube to define two separate fluid conveyance lumens; etc. As the fluid introduction and removal elements introduce and remove fluid from the local environment, they have distal openings that are positioned on the device upstream or distal from the ascending aorta occlusion element. Depending on the particular configuration of the device, the distal openings of the fluid introduction and removal elements may or may not be positioned at the same location relative to the target valve.

The fluid introduction element is further characterized by having a proximal end that is either directly, or through a linking fluid conveyance structure, attached to a source of a dissolution fluid, e.g., a reservoir having a volume of dissolution fluid present therein, such that the interior of the fluid introduction means is in fluid communication with a volume of dissolution fluid. The proximal end of the fluid introduction element typically includes a valve or other flow control means for controlling the amount of the fluid that enters the lumen of the fluid introduction element from the reservoir of dissolution fluid.

The fluid removal or aspiration element is further characterized in that the fluid removal element is attached at its distal end, either directly or through a fluid conveyance linking element, e.g., tube, to a reservoir for waste fluid. In addition, a negative pressure element that provides for suction of fluid from the isolated local environment at the distal end of the fluid removal element into the fluid removal element is also present, where representative negative pressure elements include pumps, vacuums, etc.

In addition to the above fluid introduction and removal elements, in certain representative embodiments the subject devices include a second fluid introduction element for introducing a second fluid into the isolated local environment of the target valve, where the second fluid delivery element is often an element for delivering a dissolution fluid attenuating fluid. When present, the second fluid delivery element may be positioned or configured relative to the above-described first fluid delivery and removal elements in a number of different ways. For example, the second fluid delivery element may be a separate tube or analogous structure, where the tube may or may not be present in one or more of the first fluid delivery element or aspiration element, or vice versa, e.g., the different elements may be concentric with each other. Alternatively, the second fluid delivery element may be a lumen present in a multi-lumen structure, where other lumens may be the aspiration and/or first fluid delivery elements.

The second fluid introduction element is further characterized by having a proximal end that is attached, either directly or through a linking fluid conveyance structure, to a source of a second fluid, e.g., a reservoir having a volume of dissolution fluid attenuating fluid present therein, such that the interior of the second fluid introduction means is in fluid communication with a volume of dissolution fluid attenuating fluid. The proximal end of the fluid introduction element typically includes a valve or other flow control element for controlling the amount of the fluid that enters the lumen of the second fluid introduction element from the reservoir of dissolution fluid attenuating fluid.

Additional General Features of the Device

In certain embodiments, the device may include a fluid flow modulator which, upon deployment of the device, modifies blood flow exiting the shunt into the aorta. A representative embodiment of such an element is further described in connection with the description of the specific embodiment depicted in FIGS. 4 and 5, below.

In certain embodiments, the device may include an integrated particle capture element, e.g., mesh, netting or other suitable structure, that can prevent particles, tissue debris or other undesired structures that may be produced during practice of the subject methods to enter the systemic vasculature of the subject or patient.

In certain embodiments, the devices may include an integrated introducer element. The integrated introducer element is characterized by being capable of assuming first and second configurations depending on the particular time point during deployment, such that at an initial time point during entry of the device into the vascular it is contiguous with the distal end of the device, e.g., where the above described valve isolation, flushing and shunt elements are positioned. At a second time period as the distal end is progressed to the remove valve site, the distal end separates from the introducer element, such that the integrated introduce and distal end of the device are no longer contiguous. A representative embodiment of such a device is further described in connection with FIGS. 6A and 6B, below. While such an integrated introducer element is described in this application primarily in connection with the particular catheter devices described herein, it is to be understood that this integrated introducer element is readily adaptable to other catheter devices that benefit from introduction by use of an introducer, and such other catheter devices modified to have an integrated introducer element fall within the scope of certain embodiments of the invention. As such, certain embodiments of the invention have a scope sufficiently broad to include any catheter device that is modified to include an integrated introducer element.

The device may be a device in which all of the elements are statically positioned relative to each other such that no relative movement is possible between any two elements of the device, or two or more of the subject elements may be movable relative to each other in the device. For example, the fluid introduction element may be slidably positioned inside of the fluid removal element; the ventricular side occlusion means may be adjustably movable relative to the remainder of the device to provide for an adjustable isolated local environment; etc.

The components of the subject devices, as described above, may be fabricated from any convenient material. The materials must be able to withstand contact with any fluids introduced or removed thereby and should be physiological compatible, at least for the period of time in which they are being used. Suitable materials include biocompatible polymers, e.g. polyimide, PBAX™, polyethylene, and the like. Any glues or fittings that are employed must also be able to meet the same criteria. Any convenient fabrication protocol may be employed, where numerous suitable protocols are known to those of skill in the art.

Representative Specific Embodiment

A representative embodiment of the subject devices is depicted in FIG. 1. Percutaneous catheter device 10 includes ventricular side occlusion balloon 12 and aortic side occlusion "bell" 14. The device further includes shunt 16 that has distal inflow ports 16a and proximal outflow ports 16b covered by one-way valves 16c. Not shown is the isolated valve-flushing element, that comprises fluid inflow and outflow lumens housed in structure 18. During delivery, the distal end of the device can be retracted into sheath 19 for a suitable low-profile for delivery to the target site. As evidenced from the depiction, the device is configured and dimensions to isolate an aortic valve following percutaneous delivery of the distal end of the device to the target valve site via the vasculature. A variety of specific dimensions for the device and components thereof may be chosen to meet the above general parameters, and such dimensions are readily determined by those of skill in the art.

Figure 2:
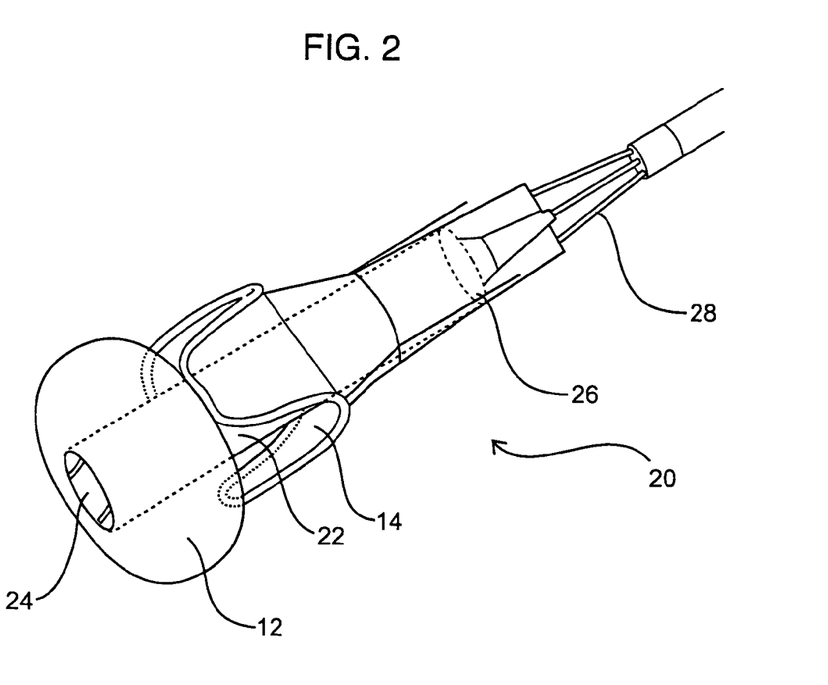
FIG. 2 provides an illustration of an alternative representative device configuration according to the subject invention.

An alternative specific embodiment have a modified shunt/valve configuration is depicted in FIG. 2. In FIG. 2, device 20 includes certain features that are the same as those shown in the device depicted in FIG. 1. For example, device 20 includes a ventricular side balloon 12 and an isolation bell 14. However, shunt element 16 has been replaced with a modified shunt element 22 which has a single distal opening for blood inflow 24 and a single proximal fluid outflow port 26 through which fluid flow is modulated or controlled by an integral one-way valve, not shown. As depicted in this embodiment, the valve element is much closer to the isolation bell than it is in the device shown in FIG. 1. In the device shown in FIG. 2, fluid flow lumens 28 are clearly visible proximal to the isolation bell.

Yet another specific embodiment of the device is shown in FIG. 3, which is a further variation of the device shown in FIG. 2. In FIG. 3, device 30 differs from device 20 in FIG. 2 in that the ventricular side occlusion balloon has been replaced by an occlusion funnel element 32, which is positioned at the distal end of the shunt and serves to anchor the distal end of the device as the target site.

Yet another specific embodiment of the device is shown in FIG. 4, which is a further variation of the device shown in FIG. 3. In FIG. 4, device 40 differs from device 30 in FIG. 3 in that the distal end of the device further includes a fluid flow diverter 42. Flow diverter 42 is a conical tipped element which provides for a number of advantages. During introduction of the distal end of the device to the target site, the flow diverter 42 is contiguous with a delivery sheath 44 as shown in FIGS. 5 and 6, such that the device has a blunt end which provides for various advantages during delivery, such as reduced collateral tissue damage. During use of the subject device when the target valve is isolated is blood in shunted from the ventricle to the aorta, the flow diverter 42 may be retracted to a position proximal the blood outflow port of the shunt, and thereby divert flow away from the device and provide for improved blood flow in the aorta and rest of the vasculature.

Methods

The above-described devices find use in methods of flushing an aortic valve with at least one fluid composition. In the broadest sense, the subject catheter systems may be employed to introduce any active agent in a fluid delivery vehicle to an aortic valve by flushing the aortic valve with such a fluid composition. The subject systems achieve local delivery of active agents in fluid delivery vehicles by irrigating or flushing an isolated aortic valve with the fluid agent composition.

Of particular interest are methods of using the subject devices to percutaneously flush an isolated aortic valve of a beating heart, particularly a stenotic aortic valve, with a dissolution fluid, where the dissolution fluid may be an organic matter dissolution fluid or an inorganic matter dissolution fluid, or a fluid that is capable of both inorganic matter and organic matter dissolution. Representative dissolution fluids are In U.S. Pat. No. 6,533,767; the disclosure of which is herein incorporated by reference.

In many embodiments, the dissolution fluid employed in the subject methods is an inorganic matter dissolution solution. In many of these embodiments, the inorganic matter dissolution fluid is an acidic dissolution fluid. A variety of different types of acidic dissolution solutions may be employed in the subject methods. The acidic treatment solutions that find use in the subject methods generally have a pH of less than about 6.5, where the pH is usually less than about 4.0 and more usually less than about 3.0. In representative embodiments, the pH ranges from 0 to 2, and usually 0 to 1. The acidic treatment solution can include a number of different types of acids, where the acids may or may not include a hydrocarbon moiety, i.e., a hydrogen bonded directly to a carbon atom. Suitable acids that lack a hydrocarbon moiety include halogen acids, oxy acids and mixtures thereof, where specific acids of interest of this type include, but are not limited to, hydrochloric, nitric, sulfuric, phosphoric, hydroboric, hydrobromic, carbonic and hydroiotic acids. For such acids, the acid can be a concentrated acid, or can be diluted. Upon dilution, the concentration of an inorganic acid will generally be from about 10 N to about 0.01 N, preferably between 5 N to 0.1 N. Also of interest are acids that include a hydrocarbon moiety, where such acids include, but are not limited to, any organic acid of one to six ($C_1$ to $C_6$) carbons in length. Organic acids of this type include, but are not limited to, formic, acetic, propionic, maleic, butanoic, valeric, hexanoic, phenolic, cyclopentanecarboxylic, benzoic, and the like. For an organic acid, the acid can be in concentrated form, or can be diluted. The acidic treatment solution can be composed of either a monobasic or a polybasic acid. Acids are "monobasic" when they have only one replaceable hydrogen atom and yield only one series of salts (e.g., HCl). Acids are "polybasic" when they contain two or more hydrogen atoms which may be neutralized by alkalies and replaced by organic radicals.

In many embodiments of the subject invention, the acid solution is hypertonic, by which is meant that the osmolarity of the solution is greater than that of whole blood, i.e. the osmolarity is greater than 300 mosmol. The solution may be rendered hypertonic by including any convenient component or components in the solution which provide for the desired elevated osmolarity.

Any convenient agent that is capable of increasing the osmolarity of the solution may be employed, where suitable agents include salts, sugars, and the like. In many embodiments, the agent that is employed to render the solution hypertonic is one or more, usually no more than three, and more usually no more than two, different salts. Generally, the salt concentration in these embodiments of the solution is at least about 100 mosmol, usually at least about 200 mosmol and more usually at least about 300 mosmol, where the concentration may be as high as 3000 mosmol or higher, depending on the particular salt being employed to render the solution hypertonic, where the solution may be saturated with respect to the salt in certain embodiments. Salts that may be present in the subject solutions include: NaCl, $MgCl_2$, Ringers, etc. where NaCl is preferred in many embodiments.

Of particular interest in many embodiments is the use of a hydrogen chloride solution. In hydrogen chloride solutions that find use in the subject invention, the concentration of HCl in the solution ranges from about 0.001 to 1.0 N, usually from about 0.01 to 1.0 N and more usually from about 0.1 to 1.0 N. In many embodiments, the hydrogen chloride solution will further include one or more salts which make the solution hypertonic, as described above. In certain preferred embodiments, the salt is NaCl, where the concentration of NaCl in the solution is at least 0.05 M, usually at least 0.10 M, and more usually at least 0.15 M, where the concentration may be as high as 0.25 M or higher. In certain embodiments, the solution will be saturated with NaCl.

Of particular interest are aqueous hydrogen chloride solutions that consist of water, hydrogen chloride and NaCl. The concentration of hydrogen chloride in these solutions of particular interest ranges from about 0.01 to 1.0 N, usually from about 0.05 to 0.5 N and more usually from about 0.075 to 0.25 N. The concentration of NaCl in these solutions of particular interest ranges from about 0.05 to 0.25 M, usually from about 0.05 to 0.10 M.

In certain embodiments of the subject methods, e.g., those embodiments in which a device having two fluid delivery elements, in addition to the dissolution solution, the target aortic valve is also contacted with a dissolution solution attenuating fluid. The nature of the dissolution solution attenuating fluid necessarily depends on the nature of the dissolution fluid, where representative pairs of fluids and their attenuating counterparts are described in U.S. Pat. No. 6,533,767, the disclosure of which is herein incorporated by reference.

Where the dissolution fluid is an acidic dissolution fluid, attenuating fluids of particular interest are pH elevating fluids. By pH elevating solution is meant any solution that, upon combination with the acidic dissolution solution, produces a solution with an elevated pH with respect to the acidic dissolution solution. In principle, any fluid that, upon combination of with the acid dissolution fluid produces a solution having a pH higher than that of the acidic dissolution fluid, may be employed, so long as the fluid is biocompatible, at least for the period of time that it is present in the target vascular site. The pH elevating solution should have a pH of at least about 4, usually at least about 6 and more usually at least about 8. As such, pH elevating fluids of interest include water, physiological acceptable buffer solutions, etc., where in many embodiments, the pH elevating solution is a buffer solution. Representative buffer solutions of interest include: phosphate buffered saline, sodium bicarbonate and the like.

In practicing the subject methods, the first step is to prepare the host or patient for the procedure. Following preparation of the host/patient/subject, the device is placed in position such that, upon deployment, the target aortic valve can be isolated from the remainder of the vasculature with the device.

To place the device in position, the device is percutaneously introduced to the target site from a remote site, e.g., via femoral access, as is known in the art. The device may be introduced over a guide wire. The percutaneously introduced device is advanced in a retrograde fashion such the distal end of the device extends through the aortic valve into the left ventricle. Following proper positioning of the distal end of the device into the left ventricle, the isolation elements of the device are then deployed in a manner sufficient to substantially, if not completely, isolate the to be treated aortic valve from the remainder of the vasculature of the host. The particular manner of deployment necessarily depends on the nature of the isolation system of the device. For example, where the ventricular side occlusion element of the isolation system of the device is an inflatable balloon, the isolation step includes a step of inflating the balloon. Where the aortic side isolation element is an expandable aortic isolation element, the isolation step includes a step of expanding the aortic side isolation element. Isolation of the valve results in blood flow through the shunt element under the force of the still beating heart.

The above protocol results in an isolated target aortic valve. Following isolation of the aortic valve, the isolated aortic valve is then flushed with at least the dissolution fluid, e.g., an acidic dissolution fluid. As the isolated valve is flushed with the dissolution fluid, it is dynamically contacted with the dissolution fluid. By "dynamically contact" is meant that the fresh dissolution solution is contacted with the surface of valve one or more times, including continuously, during the treatment period. In certain embodiments of the subject methods, the surface of the valve is continuously contacted or flushed with the acidic dissolution fluid. In other words, the acidic dissolution fluid is introduced in a manner such that a continuous flow of the acidic dissolution fluid across the surface of the valve is achieved. While both the ventricular and aortic surfaces of the valve may be contacted with the dissolution fluid, in many embodiments the aortic surface and commissures are contacted with the dissolution fluid, with substantially less fluid contact of the ventricular surface of the valve, if any.

In flushing with the dissolution fluid, the pressure in the local environment which includes the aortic valve may be maintained substantially isometric. By substantially isometric is meant that the pressure in the local environment does not vary by a significant amount, where the amount of variance over the treatment period does not vary by more than about 50%, usually by not more than about 10% and more usually by not more than about 5%. In other words, the local environment remains substantially isobaric during the treatment period. Accordingly, where fluid is dynamically contacted with the surface of the aortic valve surface, fluid is also simultaneously removed from the local environment, such that the overall volume of fluid in the local environment remains substantially constant, where any difference in volume at any two given times during the treatment period does not exceed about 50%, and usually does not exceed about 10%. As such, the dissolution fluid is introduced into the local environment of the isolated valve in a manner such that the local environment remains substantially isovolumetric.

When flushing the aortic valve with the dissolution fluid, the dissolution fluid is introduced in a manner such that the flow rate of the dissolution solution through the local environment is generally at least about 10 cc/min, usually at least about 20 cc/min and more usually at least about 60 cc/min, where the flow rate may be as great as 120 cc/min or greater, but usually does not exceed about 1000 cc/minute and more usually does not exceed about 500 cc/minute, where by "volume" is meant the local environment of the isolated aortic valve, as defined above. The total amount of dissolution fluid that is passed through the local environment during the treatment period typically ranges from about 100 to 1000 cc, usually from about 200 to 800 cc and more usually from about 400 to 500 cc. The solution is generally pressurized to achieve the desired flow rate, as described supra. As such, the pressure at the distal end of the dissolution fluid delivery element through which the dissolution fluid is introduced into the local environment typically ranges from about 50 to 1200 psi, usually from about 100 to 600 psi and more usually from about 200 to 400 psi. It is important to note that the overall pressure in the local environment is maintained in certain embodiments at substantially isometric or isobaric conditions. As such, the negative pressure at the entrance to the aspiration element or fluid removal means is of sufficient magnitude to provide for substantially isobaric conditions. In certain embodiments, the overall pressure in the local environment is maintained at a value ranging from about 0.1 to 3 psi, usually from a bout 0.5 to 2.5 psi and more usually from about 1 to 2 psi.

The isolated aortic valve is flushed with at least the dissolution fluid, and in certain embodiments the dissolution fluid attenuating fluid, for a period of time sufficient to achieve the desired result. In representative embodiments, the dissolution fluid and dissolution attenuating fluid are cycled through the isolated region, with the isolated valve being flushed with the dissolution fluid first, followed by flushing with the dissolution fluid attenuating fluid. The desired result necessarily depends on the application being performed, where representative desired results are described below in the section entitled "Utility." While the period of time that the valve is flushed may vary, the period of time typically ranges from about 15 minutes to about 2 hours, usually from about 20 minutes to about 30 minutes and more usually from about 25 minutes to about 30 minutes.

Following treatment with the dissolution fluid, the isolated local environment is, in certain embodiments, flushed with a dissolution fluid attenuating fluid, e.g., a pH elevating solution.

Following flushing for the desired period of time, the device is then removed from the patient.

Figure 6A:
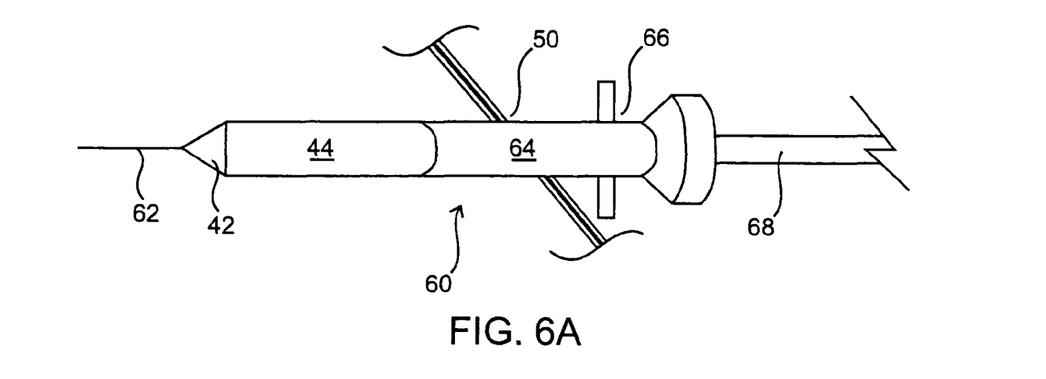
FIGS. 6A & 6B provide views of different points in the delivery of a device embodiment as depicted in FIGS. 4 and 5 that includes an integrated introducer element.
Figure 6B:
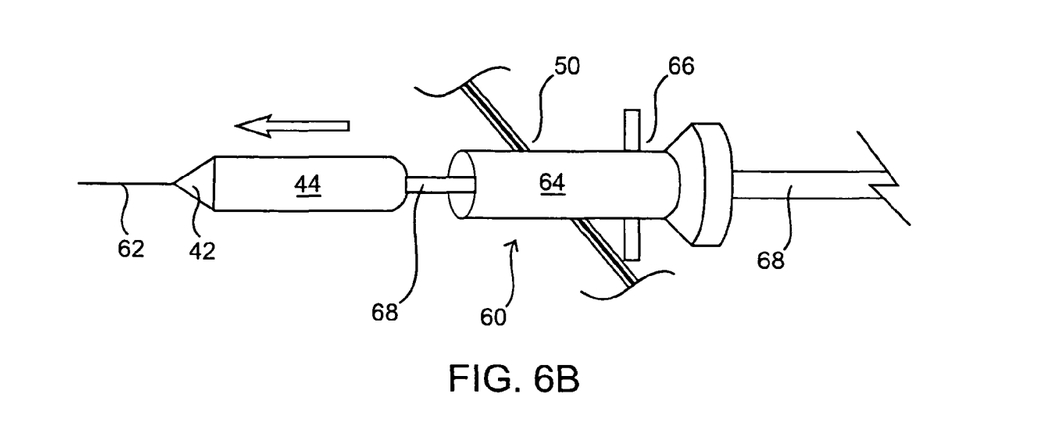

In certain embodiments, a device with an integrated introducer, such as the device depicted in FIGS. 6A and 6B, may be employed. In the device shown in FIGS. 6A and 6B, device 60 is shown being introduced into a patient at access point 50. Device 60 includes sheath element 44 in which is housed the distal end elements of the device, fluid diverter element 42, guidewire 62 and introducer 64, which include hemostasis element 66. Central lumen or catheter 68 provides fluid communication between the distal end of the device and fluid reservoirs, aspiration elements, steering mechanisms and other device control elements present at the proximal end of the device and outside of the patient. In FIG. 60, sheath 44 and introduce 64 are shown in a contiguous configuration, which is the configuration employed to initially introduce the device into the vascular system of the patient by access point 50. As the distal end of the device is moved in the direction of arrow 69 to the target valve site, sheath 44 and introducer 64 separate from each other.

Optional Method Steps

In a number of embodiments of the subject methods, the above-described methods may be modified to include a number of additional method steps. Additional method steps that may be present in the overall process include: rendering the local environment of the isolated aortic valve bloodless, washing or rinsing the isolated local environment of the aortic valve, applying external energy to the aortic valve during treatment; imaging the isolated vascular site; and the like.

Rendering the Local Environment Bloodless

In many preferred embodiments, as described above, the local environment of the aortic valve is rendered substantially bloodless prior to introduction of the acidic dissolution fluid. In these embodiments, the isolation system is deployed to physically isolate the local environment from the remainder of the circulatory system and then the local environment is flushed with a physiologically acceptable solution, such that substantially all of the blood present in the solution is removed. Typically, a washing solution will be employed in this step of rendering the local environment bloodless. Examples of washing solutions that may find use in these embodiments include: water for injection, saline solutions, e.g. Ringer's, phosphate buffered saline, or other physiologically acceptable solutions. The washing solution may include an anti-clotting factor in many embodiments, where anticlotting factors of interest include heparin and the like. The washing solution can also contain chelating agents.

Application of External Energy

In certain embodiments, external energy is applied to the target aortic valve to promote mechanical break-up of the calcified deposits into particles or debris that can be easily removed from the vascular site. Any means of applying external energy to the aortic valve may be employed. As such, jets or other such means the device which are capable of providing varying external forces to the target deposits cause the target deposit to break up or disrupt may be employed. Of particular interest in many embodiments is the use of ultrasound. The ultrasound can be applied during the entire time of contact of the cardiovascular tissue with the acidic treatment solution, or the ultrasound can be applied for only part of the treatment period. In one embodiment, ultrasound is applied for several short periods of time while the dissolution treatment solution is contacted with the target occlusion. There are several devices for the application of ultrasound to cardiovascular tissue known to those of skill in the art. See e.g. U.S. Pat. No. 4,808,153 and U.S. Pat. No. 5,432,663, the disclosures of which are herein incorporated by reference.

Another means that may be employed to apply external energy to the lesion during the dissolution process is to use a mechanical means of applying external energy. Mechanical means of interest include moving structures, e.g. rotating wires, guidewires, which physically contact the target occlusion and thereby apply physical external energy to the target lesion.

Imaging

In addition, it may be convenient to monitor or visualize the vascular site prior to or during treatment. A variety of suitable monitoring means are known to those of skill in the art. Any convenient means of invasive or noninvasive detection and/or quantification may be employed. Such means include plain film roentgenography, coronary arteriography, fluoroscopy, including digital subtraction fluoroscopy, cinefluorography, conventional, helical and electron beam computed tomography, intravascular ultrasound (IVUS), magnetic resonance imaging, transthoracic and transesophageal echocardiography, rapid CT scanning, antioscopy and the like. Any of these means can be used to monitor the vascular site before, during or after contact with the dissolution fluid.

In many embodiments, an imaging agent is employed, where the imaging agent may or may not be present in the acidic dissolution solution. Imaging agents of particular interest include: non-ionic imaging agents, e.g. CONRAY™, OXILAN™, and the like.

Utility

The above-described methods and devices find use in any application in which it is desired to contact an isolated aortic valve with a fluid, e.g., a fluid composition of a therapeutic agent. The subject devices and methods are particularly suited for use in the treatment of aortic stenosis. The term "aortic stenosis" is used broadly to refer to any condition that is characterized by disease and narrowing of the valve such that fluid flow through the valve is impeded. In many instances, the target aortic stenosis condition of the subject methods is characterized by having calcification present on the valve leaflets that reduces or impedes mobility of the leaflets. Of particular interest is the treatment of aortic stenosis characterized by calcified deposits on the leaflet surface in which the calcification results in a aortic valve flow (as measured by the cardiac catheterization technique known in the art as the gold standard for evaluating aortic stenosis) that is less then 3.0, often less than about 2.5 and more often less than about 2.0, where in many embodiments the aortic valve flow may be less than 1.0.

Treatment of aortic stenosis according to the subject invention results in at least a reduction in the amount of calcium phosphate mineral present on a stenotic valve surface, i.e., the aortic side leaflet surface. The amount of reduction that is achieve with the subject invention is typically at least about 10%, usually at least about 20% and more usually at least about 30% by weight.

In many embodiments, treatment according to the subject methods results in an increase in aortic valve flow, as determined using the cardiac catheterization protocol described above. The amount of increase that is achieve is generally at least about 0.5 units, usually at least about 1.0 unit. In many embodiments, the aortic valve flow is improved to a value that is at least about 1, preferably at least about 1.5 and more preferably at least about 2.0, where one may achieve even higher values, including the normal 3.0, in certain embodiments.

Treatment also typically results in amelioration of one or more symptoms associated with, e.g., caused by, aortic stenosis, including but not limited to: chest pain, fainting, shortness of breath, delayed upstroke and lower intensity of the carotid pulse, heart murmur, abnormal EKG patterns, etc.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g. rabbits) and primates (e.g., humans, chimpanzees, and monkeys). In many embodiments, the hosts will be humans.

Systems

Also provided by the subject invention are systems for practicing the subject methods, i.e. for flushing an aortic valve with a fluid, e.g., to treat an aortic valve stenosis as described above. The subject systems at least include the subject devices as described above, a fluid reservoir for storing acidic dissolution fluid, optionally a fluid reservoir for storing a pH elevating fluid and a negative pressure element for providing aspiration or suction during use of the system. The systems may further include a number of optional components, e.g. guidewires, pumps for pressurizing the dissolution fluid, and the like. See e.g. U.S. patent application Ser. No. 09/384,860, the disclosure of which is herein incorporated by reference.

Kits

Also provided by the subject invention are kits for use in treating a patient suffering from aortic stenosis. The subject kits at least include a device as described above. The kits may further include one or more additional components and accessories for use with the subject devices, including tubing for connecting the various components with fluid reservoirs, syringes, pumping means, etc., connectors, one or more guidewires, dilators, vacuum regulators, etc.

In certain embodiments, the kits further include one or more solutions, or precursors thereof, where in such embodiments the kits at least include an acidic dissolution fluid, such as a hydrochloric acid solution, as described above, where the solution may be present in a container(s), e.g. a flexible bag, a rigid bottle, etc. For kits that are to be used in methodologies in which the fluid is flushed through the local environment of the lesion, the amount of dissolution fluid present in the kit ranges from about 0.5 to 500 liters, usually from about 0.5 to 200 liters and more usually from about 0.5 to 100 liters. In many embodiments, the amount of dissolution fluid in the kit ranges from 0.5 to 5 liters, usually from about 0.5 to 2.0 liters and more usually from about 0.5 to 1.5 liters. Alternatively, the kit may comprise precursors of the dissolution solution for use in preparing the solution at the time of use. For example, the precursors may be provided in dry form for mixing with a fluid, e.g. water, at the time of use. In addition to the dissolution fluid or precursors thereof, the kit may further comprise one or more additional fluids (or dry precursors thereof, such as a priming solution, a washing solution, contrast medium, and the like. In many embodiments, the kits further include at least a pH elevating solution, e.g. a buffer solution such as phosphate buffered saline.

Other elements that may be present in the subject kits include various components of the systems, including manifolds, balloon inflation means, e.g. syringes, pumping means, negative pressure means etc.

In addition to above-mentioned components, the subject kits typically further include instructions for using the components of the kit to practice the subject methods with the subject devices. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

It is evident from the above discussion and results that improved methods of treating aortic stenosis are provided. The subject methods and devices provide for significant advantages in the treatment of this condition in that prosthetic elements need not be employed, as the subject's own aortic valve is maintained and restored to function. In addition, the subject methods may be less traumatic to the patent that convention valve replacement protocols. Additional advantages include a delay in the need for valve replacement. As such, the subject invention represents a significant contribution to the field.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A device comprising: (a) a valve isolation element that includes: (i) a ventricular side aortic valve occlusion element configured to prevent fluid flow from the valve to the ascending aorta, the ventricular side aortic valve occlusion element comprising a funnel structure, the funnel structure including a self-expanding ring and a thin membrane impervious to fluid flow; and (ii) an ascending aorta occlusion element, the occlusion element including an occlusion bell comprising an expandable wire scaffold; (b) a shunt element having first and second ends and configured to provide blood flow through a region of isolation proximate the aortic valve, the funnel structure being positioned at a distal end of the shunt to anchor the device in place, the shunt element passing through the central regions of the ventricular side aortic valve occlusion element and the ascending aorta occlusion element and having at least one inflow port and at least one outflow port with a one way valve; and (c) an aortic valve flushing element comprising a dissolution fluid introduction element and an aspiration element configured to maintain the volume and pressure around the valve substantially constant.

2. The device according to claim 1, wherein said fluid introducing element is in fluid communication with a source of stenotic dissolution fluid.

3. The device according to claim 2, wherein said stenotic dissolution fluid is an acidic dissolution fluid.

4. The device according to claim 1, wherein said device further includes a fluid flow diverter element.

5. The device according to claim 1, wherein said device is configured for percutaneous delivery to a target site.

6. The device according to claim 1, wherein said device further comprises an integrated introducer.

* * * * *